(12) United States Patent
Won et al.

(10) Patent No.: US 10,973,884 B2
(45) Date of Patent: Apr. 13, 2021

(54) PHARMACEUTICAL COMPOSITION FOR PREVENTING AND TREATING CANCER, CONTAINING CYB5R3 GENE OR PROTEIN AS ACTIVE INGREDIENT

(71) Applicant: KOREA RESEARCH INSTITUTE OF BIOSCIENCE AND BIOTECHNOLOGY, Daejeon (KR)

(72) Inventors: Mi Sun Won, Daejeon (KR); Hyun Seung Ban, Daejeon (KR); Bo Kyung Kim, Daejeon (KR); Soon Woo Nam, Seoul (KR); Kyeong Lee, Seoul (KR); Young-Ju Lee, Daejeon (KR); Hong-Sub Lee, Gyeonggi-do (KR); Dong Uk Kim, Daejeon (KR); Ki Cheol Park, Daejeon (KR); Joo-Young Im, Daejeon (KR); Kyoung-Jin Oh, Daejeon (KR)

(73) Assignee: KOREA RESEARCH INSTITUTE OF BIOSCIENCE AND BIOTECHNOLOGY

( * ) Notice: Subject to any disclaimer, the term of this patent is extended or adjusted under 35 U.S.C. 154(b) by 829 days.

(21) Appl. No.: 15/087,563

(22) Filed: Mar. 31, 2016

(65) Prior Publication Data

US 2016/0235821 A1 Aug. 18, 2016

Related U.S. Application Data

(63) Continuation-in-part of application No. PCT/KR2014/009204, filed on Sep. 30, 2014.

(30) Foreign Application Priority Data

Oct. 1, 2013 (KR) .......................... 10-2013-0117527

(51) Int. Cl.
| | |
|---|---|
| *A61K 38/44* | (2006.01) |
| *C12N 9/02* | (2006.01) |
| *C12N 7/00* | (2006.01) |
| *G01N 33/574* | (2006.01) |
| *A61K 48/00* | (2006.01) |

(52) U.S. Cl.
CPC ............... *A61K 38/44* (2013.01); *C12N 7/00* (2013.01); *C12N 9/004* (2013.01); *C12Y 106/02002* (2013.01); *G01N 33/57492* (2013.01); *A61K 48/005* (2013.01); *C12N 2710/10043* (2013.01); *C12N 2710/10071* (2013.01); *G01N 2333/90209* (2013.01)

(58) Field of Classification Search
CPC ..... A61K 38/44; C12N 7/00; G01N 33/57492
See application file for complete search history.

(56) References Cited

U.S. PATENT DOCUMENTS

2006/0204503 A1 9/2006 Fitchett et al.

FOREIGN PATENT DOCUMENTS

| CN | 1303926 A | | 7/2001 | |
|---|---|---|---|---|
| KR | 10-0387452 B1 | | 11/2003 | |
| KR | 10-2008-0042162 A | | 5/2008 | |
| KR | 10-2012-0002613 A | | 1/2012 | |
| WO | WO2003058021 | * | 1/2003 | ............. A61K 38/44 |
| WO | WO 2004/014314 A2 | | 2/2004 | |
| WO | WO-2005017123 A2 | * | 2/2005 | ......... C07K 14/4702 |

OTHER PUBLICATIONS

International Search Report prepared by the Korean Intellectual Property Office dated Dec. 17, 2014, for International Application No. PCT/KR2014/009204.
Lee et al. "Profiling of transcripts and proteins modulated by K-ras oncogene in the lung tissues of K-ras transgenic mice by omics approaches," International Journal of Oncology, Jan. 2009, vol. 34, No. 1, pp. 161-172.
Marin et al. "DT-diaphorase and cytochrome B5 reductase in human lung and breast tumours," British Journal of Cancer, Oct. 1997, vol. 76, No. 7, pp. 923-929.

* cited by examiner

*Primary Examiner* — Robert J Yamasaki
(74) *Attorney, Agent, or Firm* — Riverside Law LLP

(57) ABSTRACT

The present invention relates to a pharmaceutical composition for treating cancer, containing cytochrome b5 reductase 3 (CYB5R3) protein as an active ingredient. Over-expression of CYB5R3 in cancer cells results in significant reduction of hypoxia-inducible factor-1α (HIF-1α) expression, which leads inhibition of cancer cells growth in vitro and in vivo. Thus, the CYB5R3 gene or protein of the present invention can be useful as an active ingredient of a pharmaceutical composition for treating cancer.

5 Claims, 19 Drawing Sheets

Specification includes a Sequence Listing.

[Figure 1]
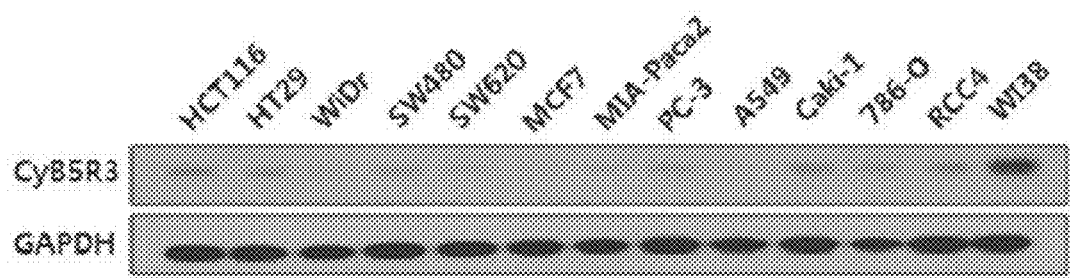
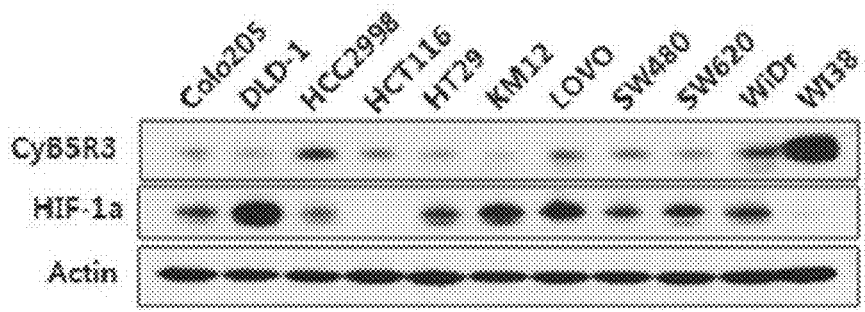

[Figure 2]
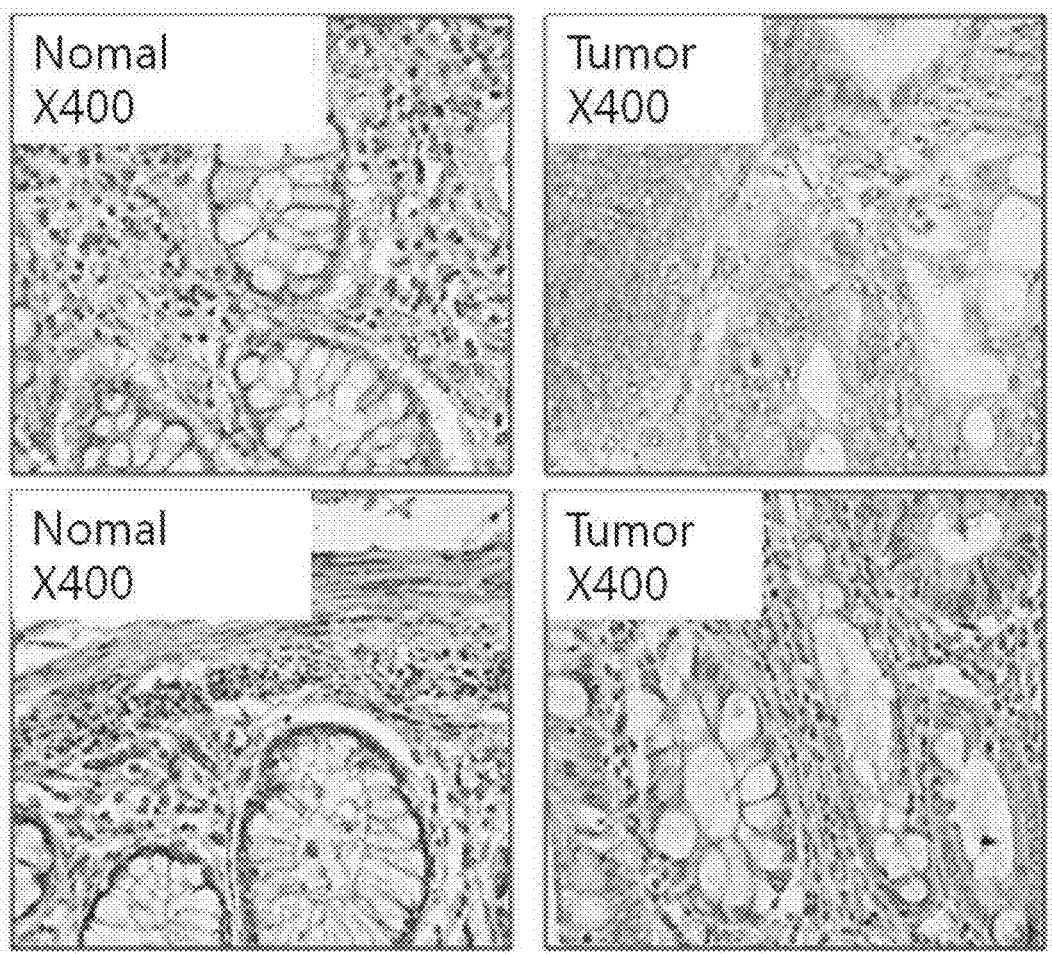

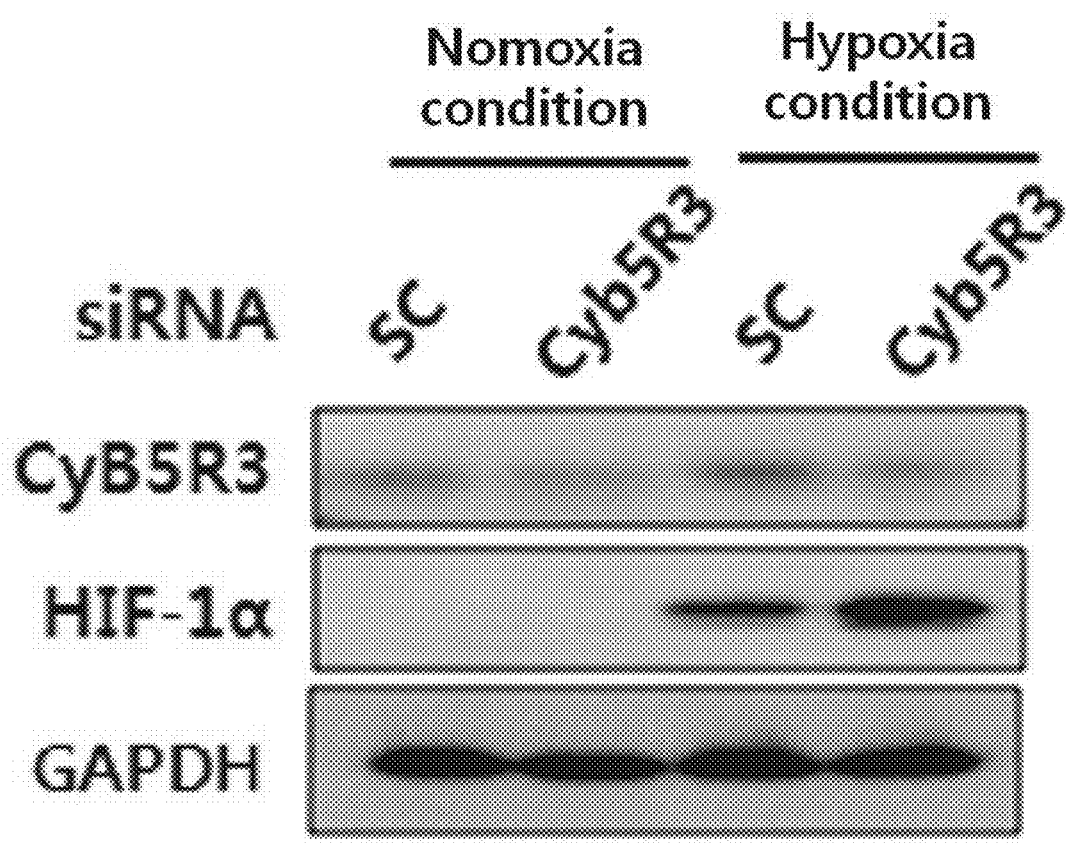
[Figure 3]

[Figure 4A]
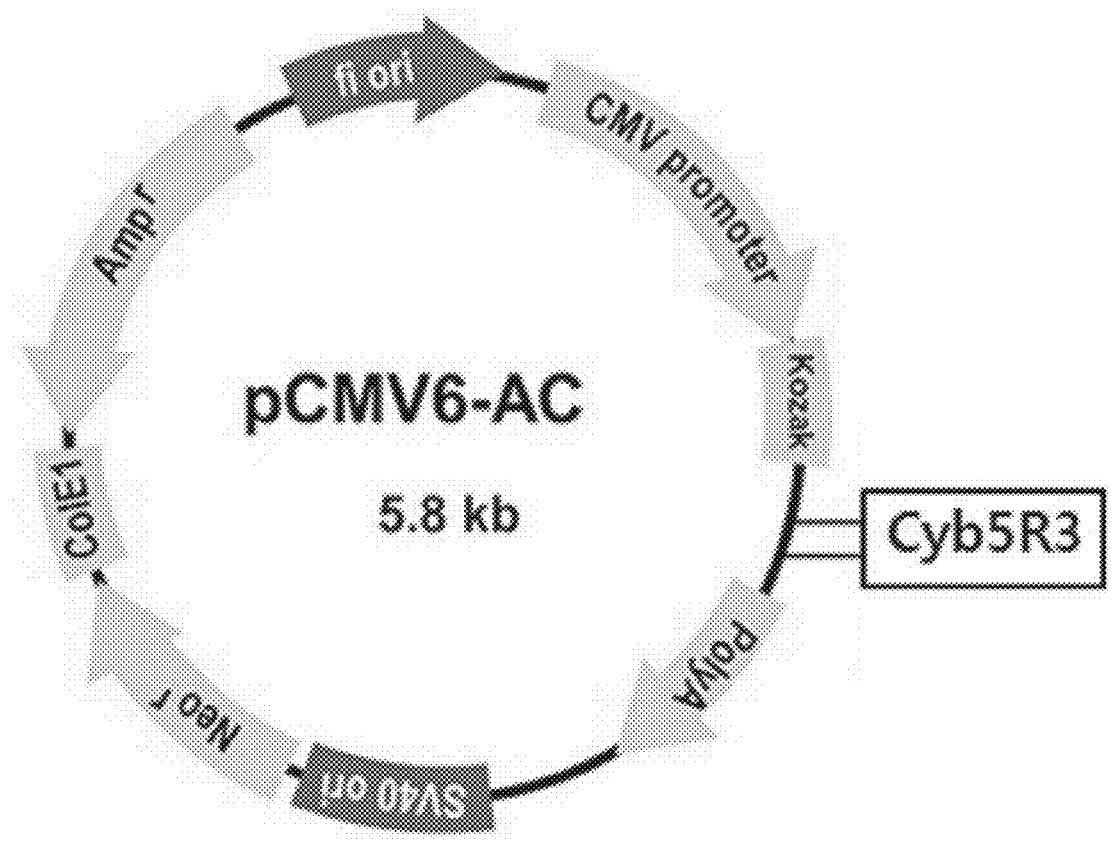

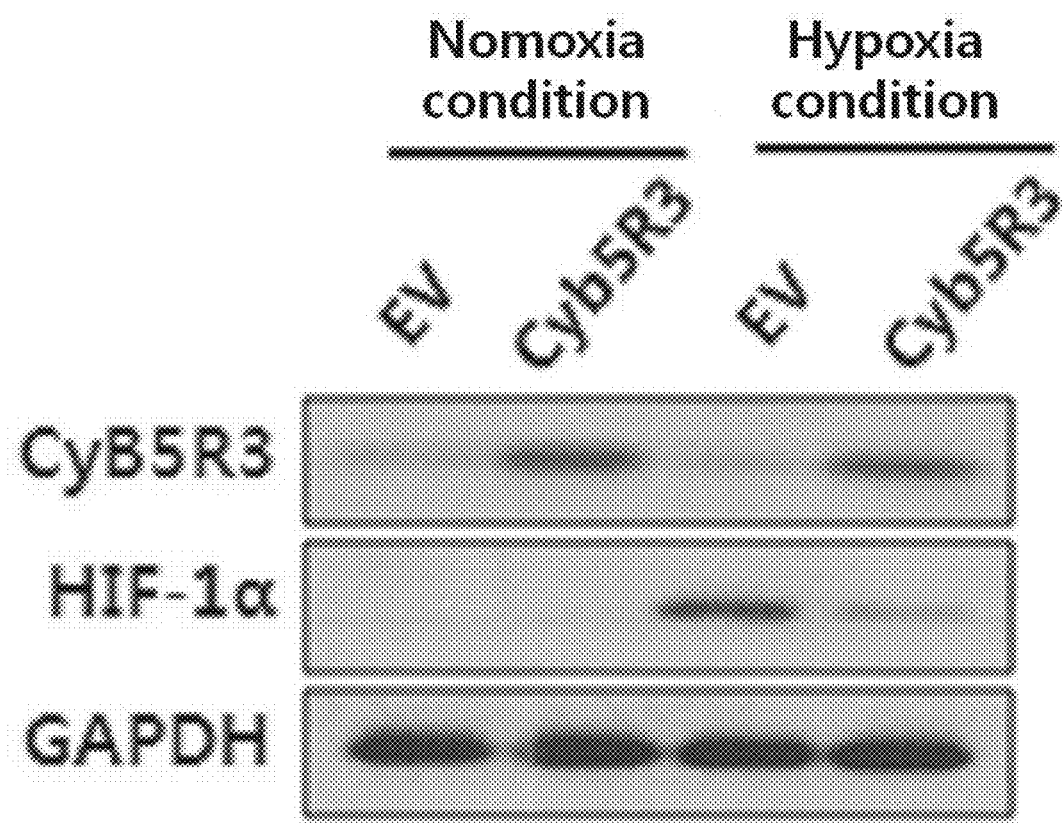

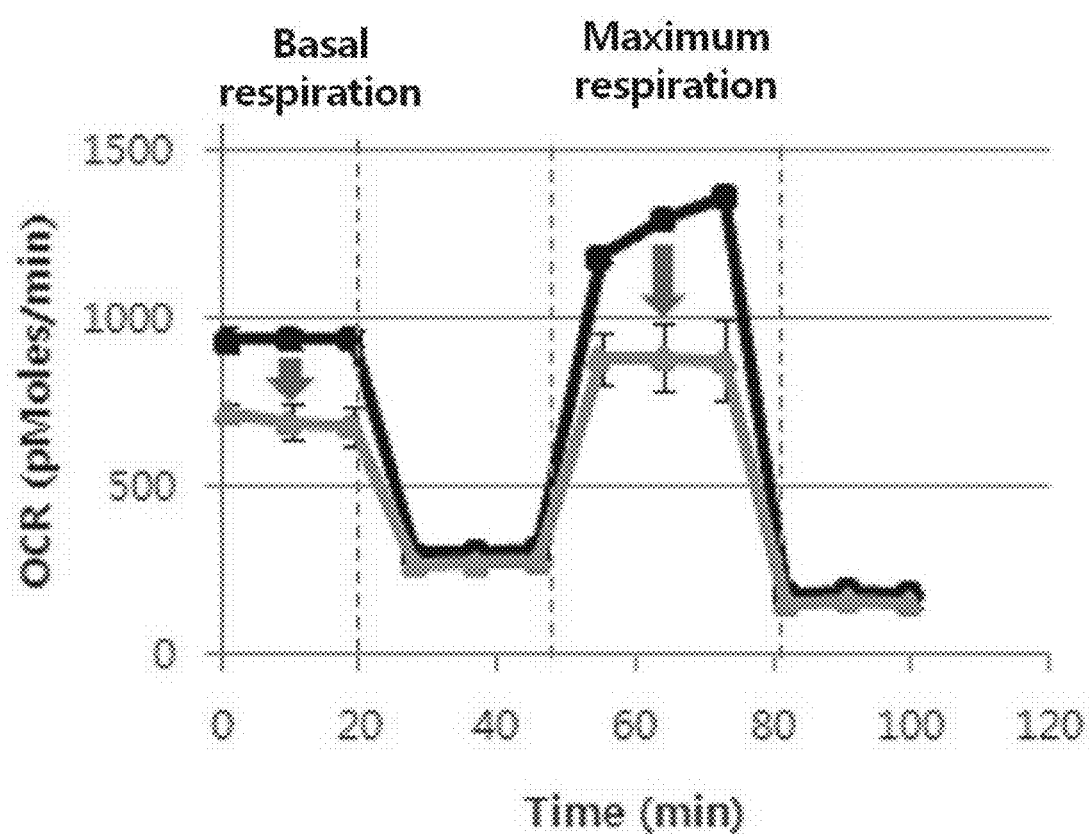
[Figure 5A]

[Figure 5B]
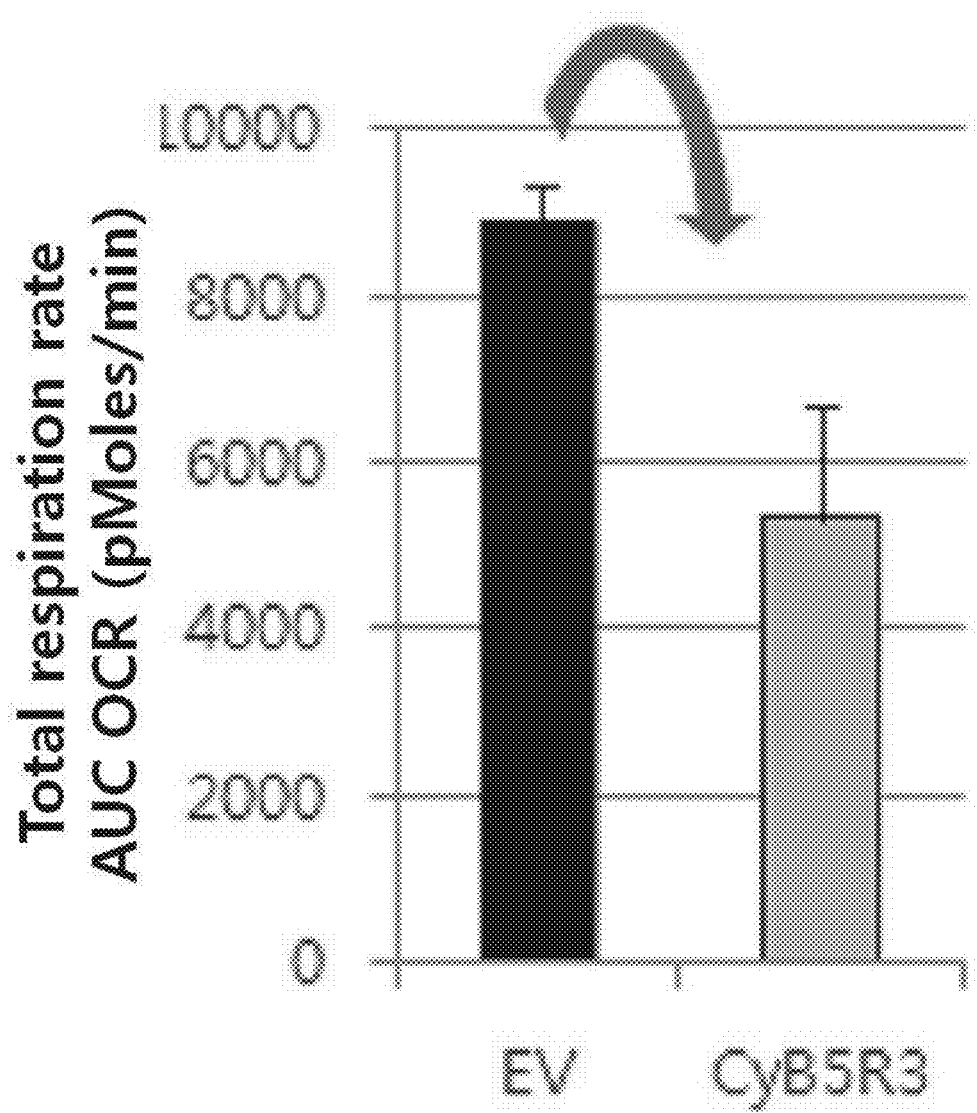

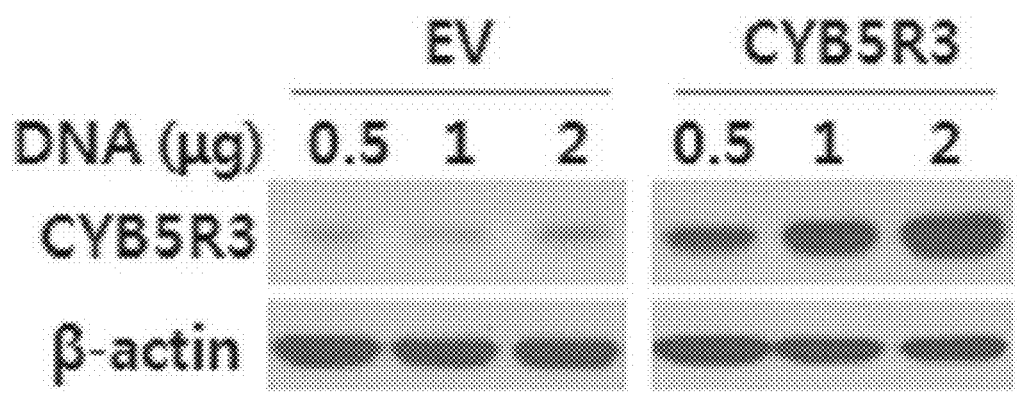
[Figure 6A]

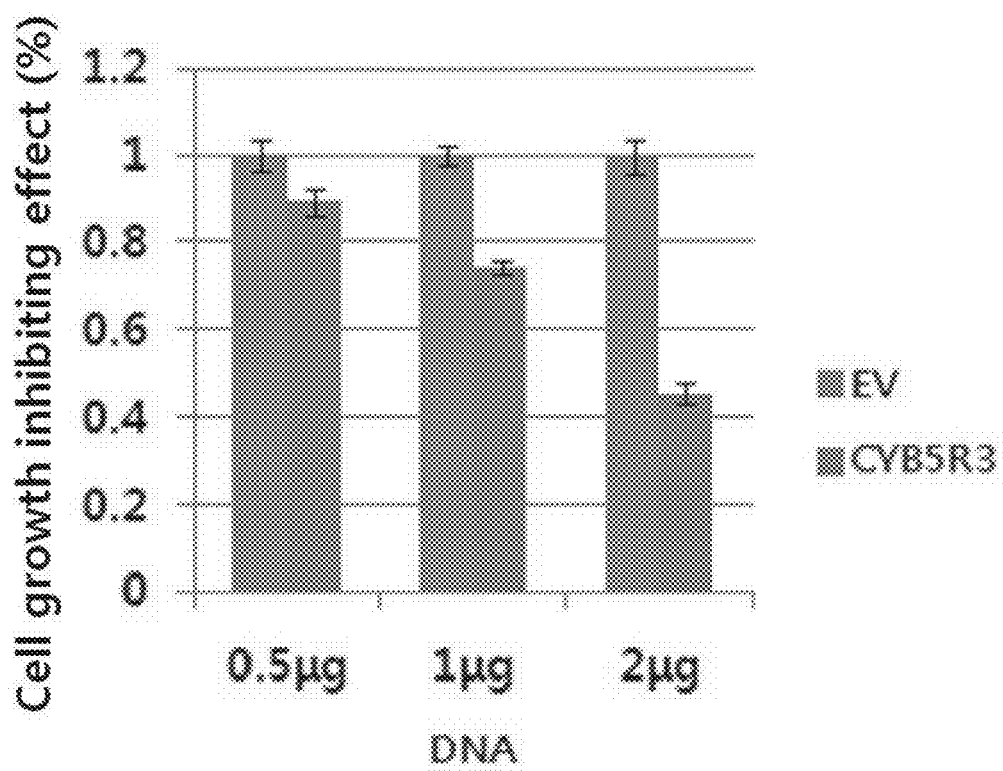
[Figure 6B]

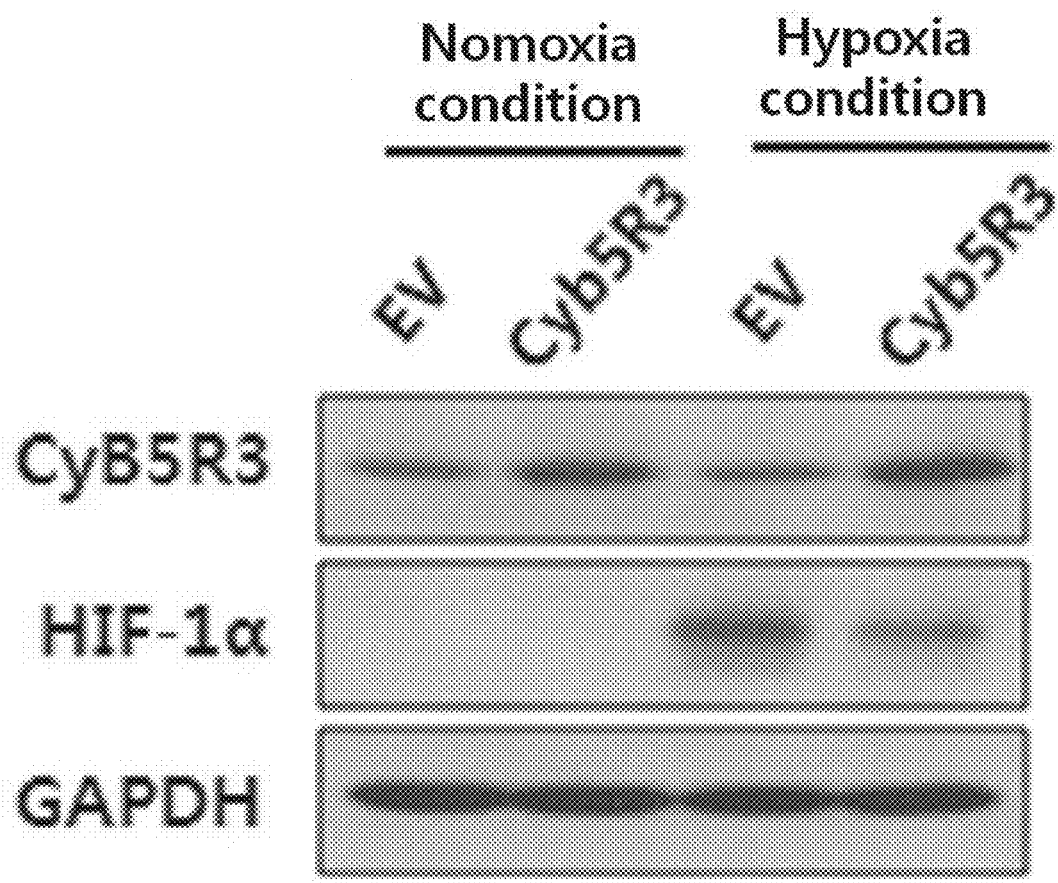
[Figure 7]

[Figure 8A]
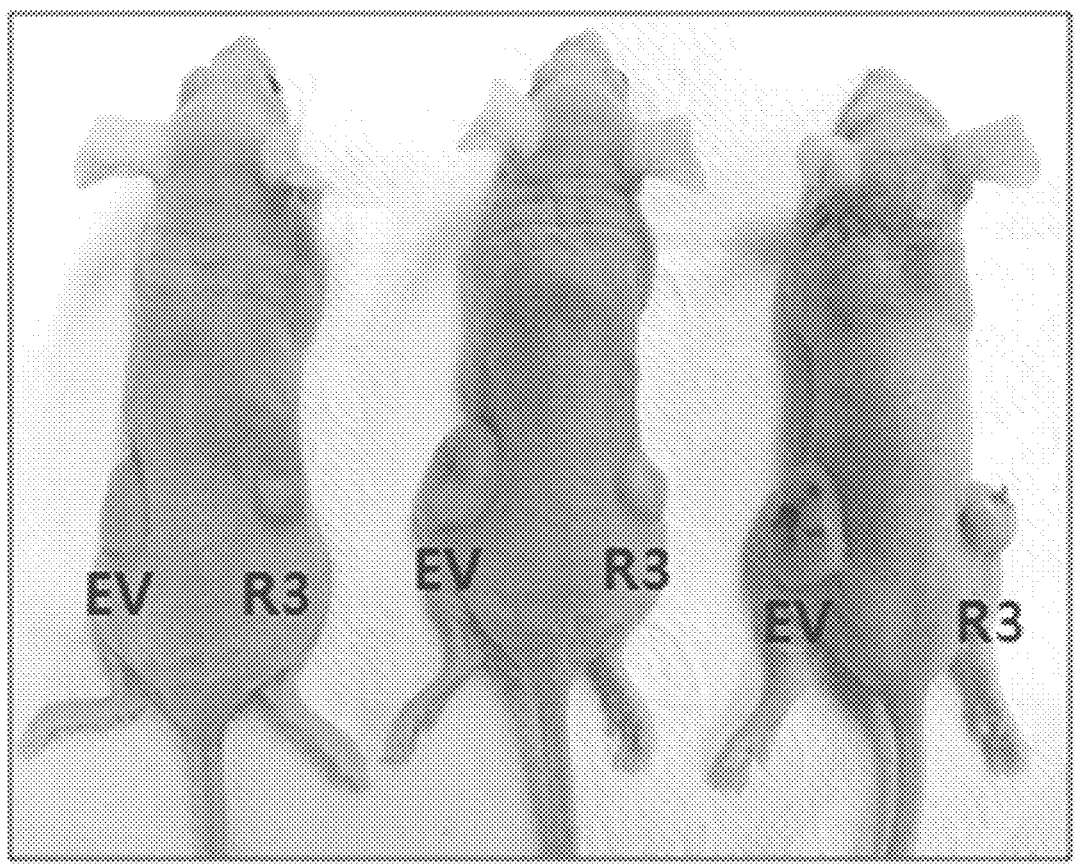

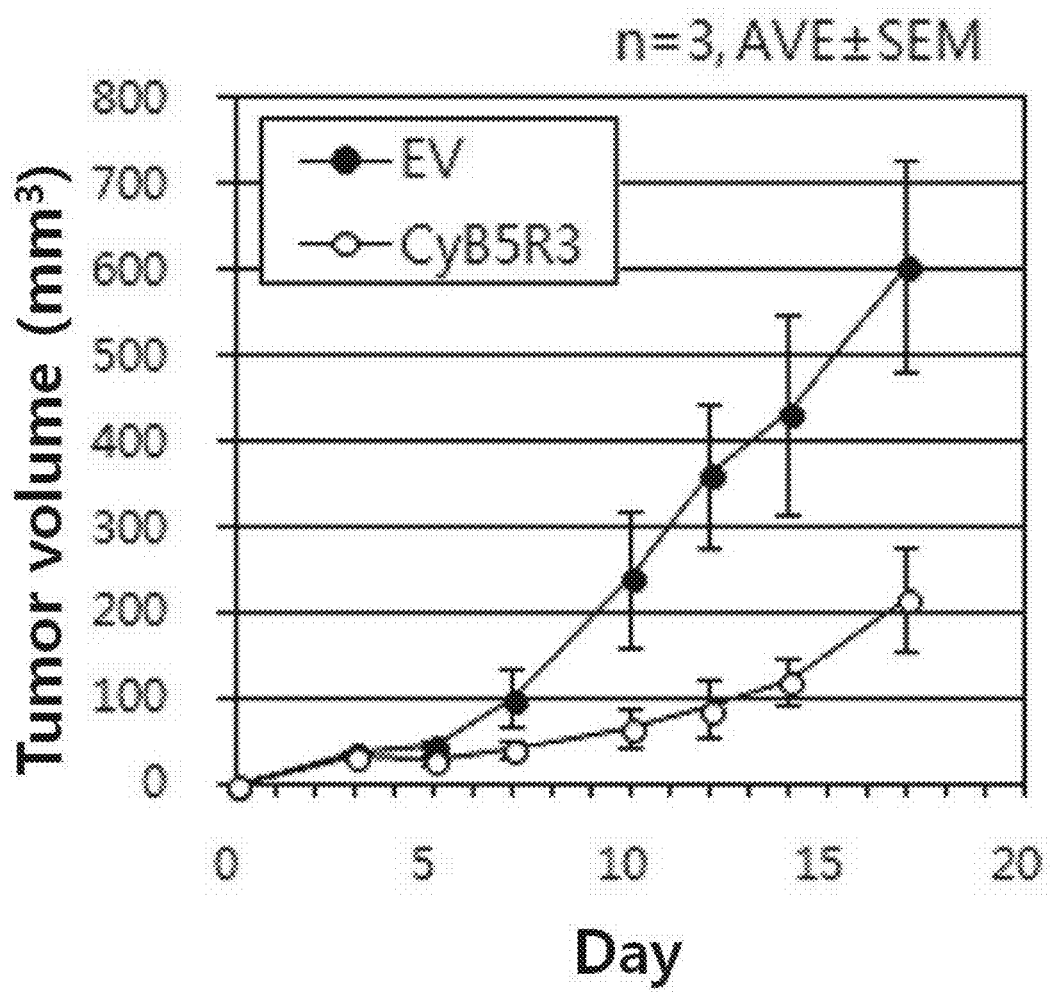
[Figure 8B]

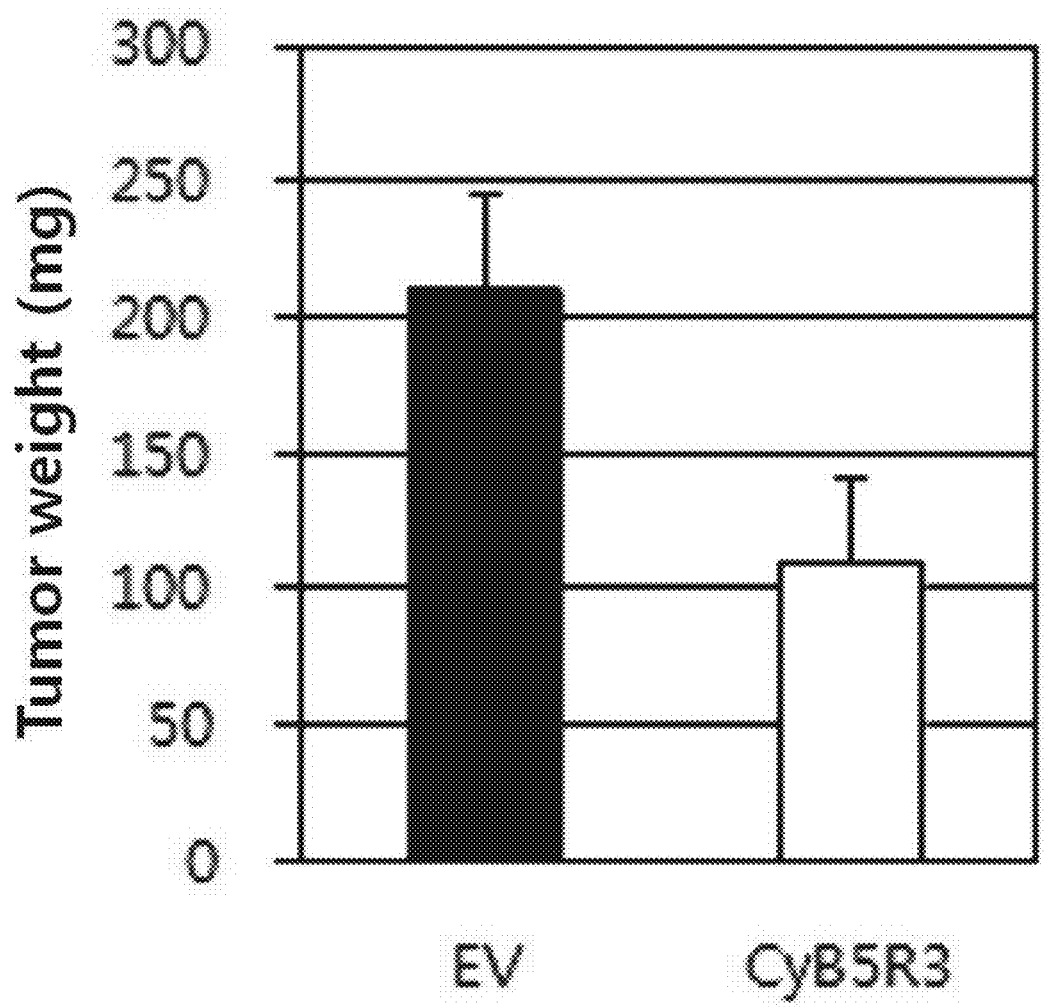
[Figure 8C]

[Figure 9]
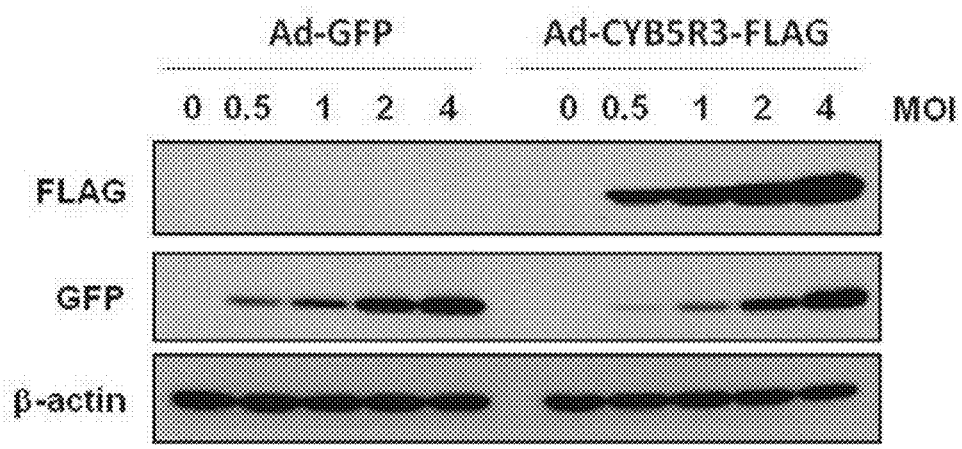

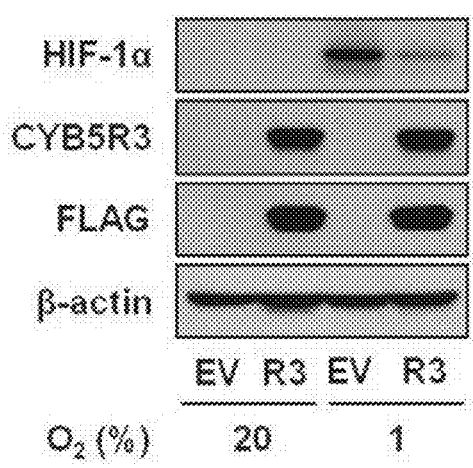
[Figure 10A]
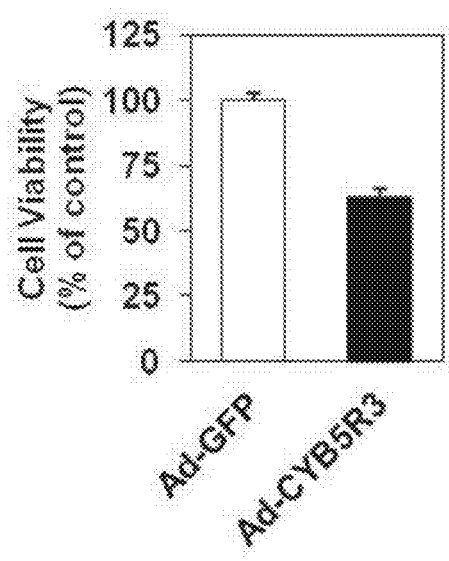
[Figure 10B]

[Figure 11A]
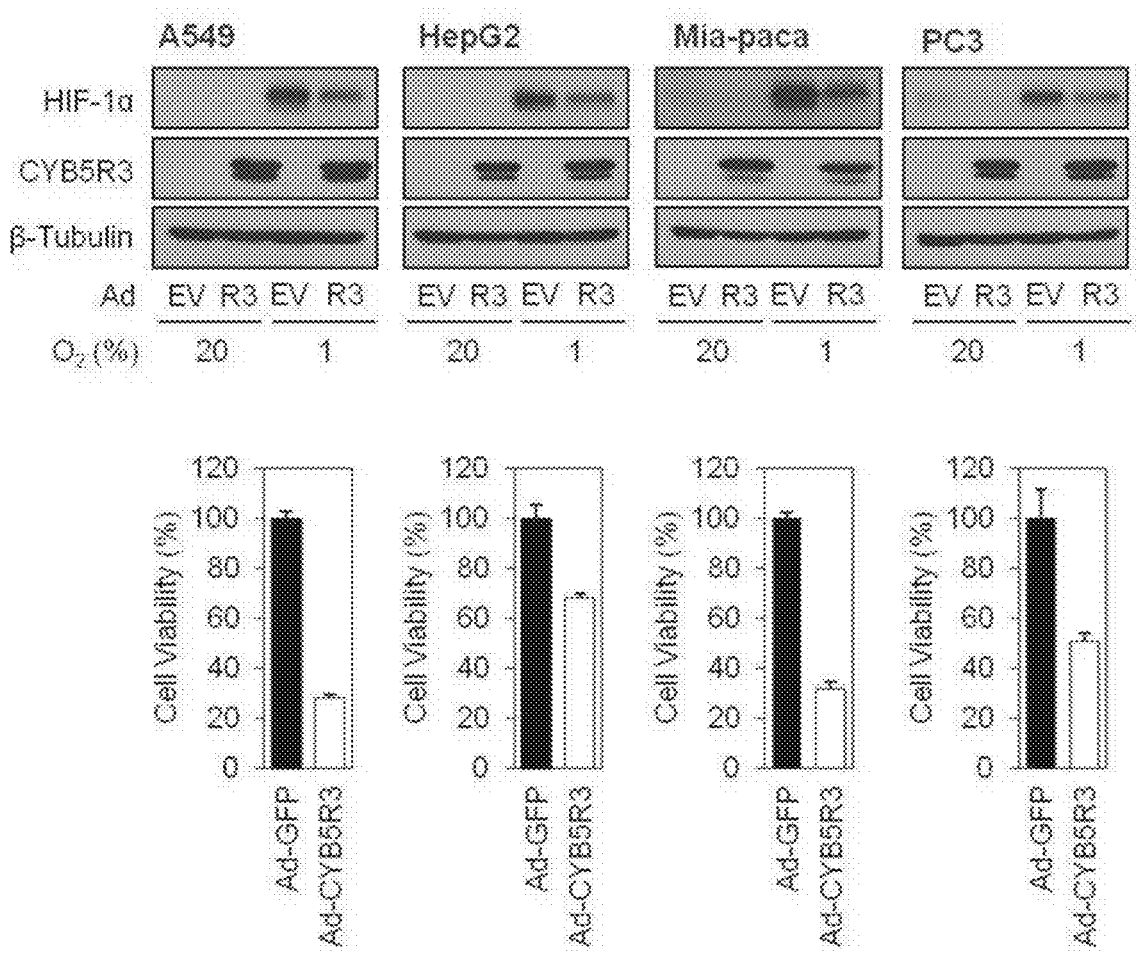

[Figure 11B]
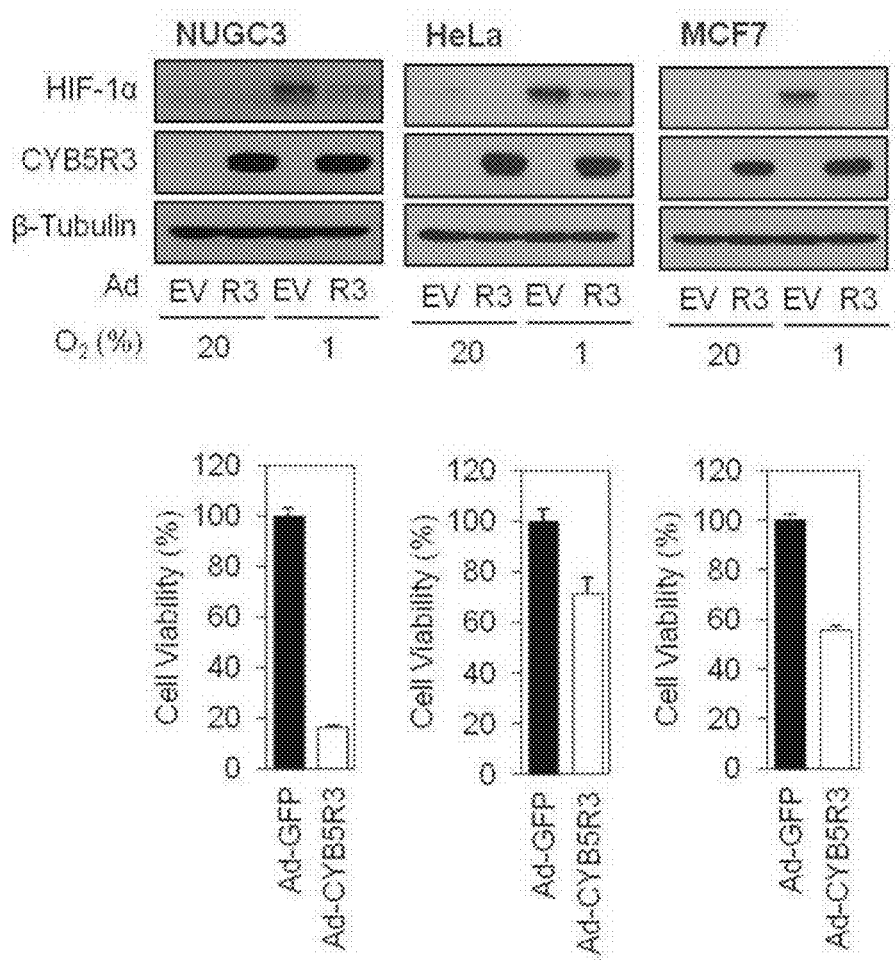

[Figure 12A]
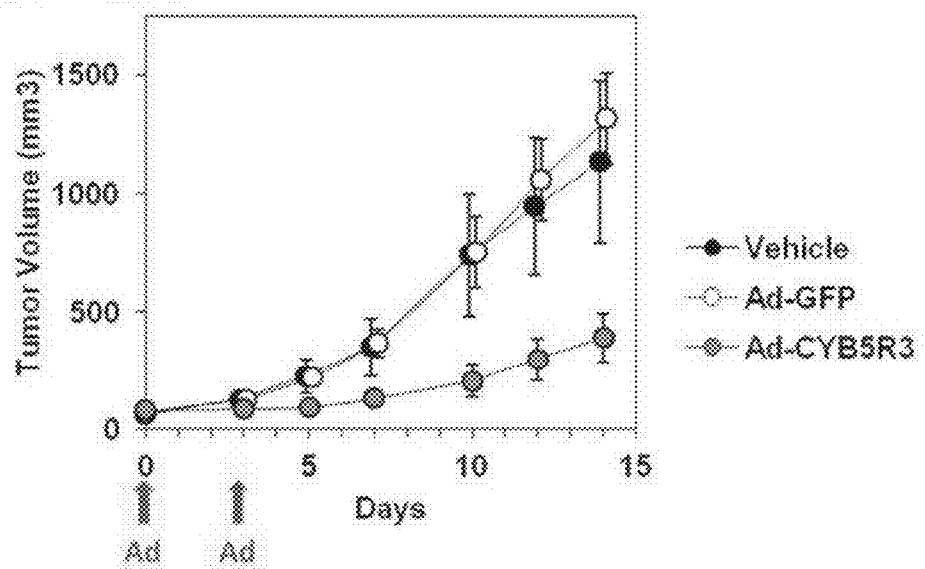
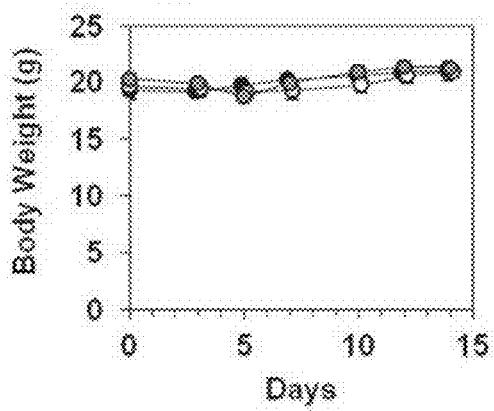
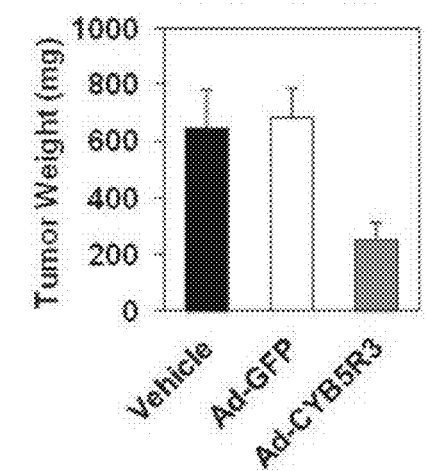

[Figure 12B]
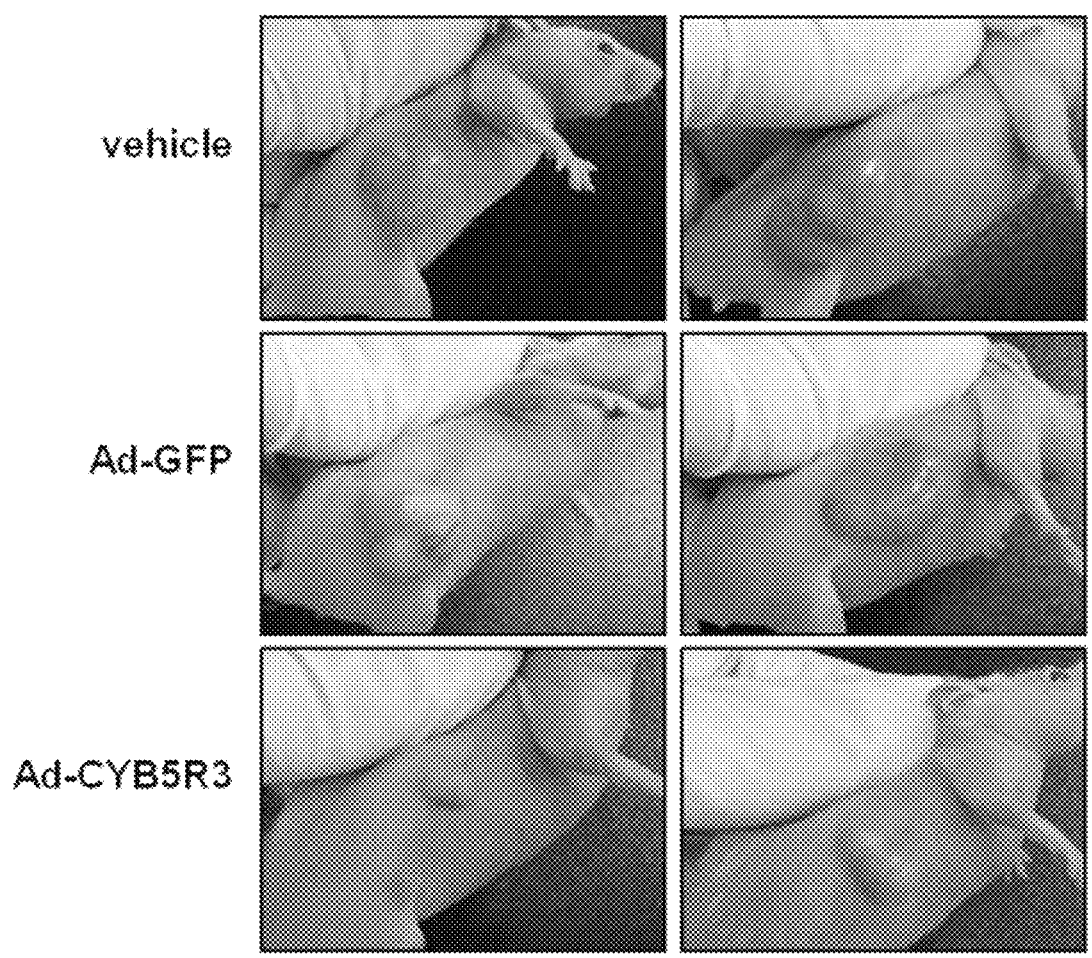
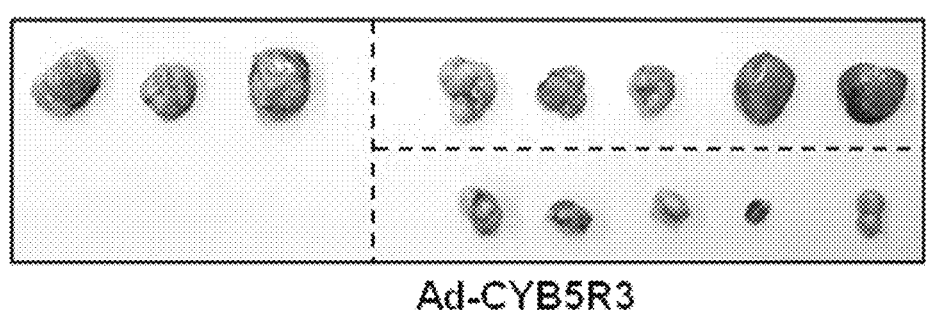

PHARMACEUTICAL COMPOSITION FOR PREVENTING AND TREATING CANCER, CONTAINING CYB5R3 GENE OR PROTEIN AS ACTIVE INGREDIENT

CROSS REFERENCE TO RELATED APPLICATIONS

This application is a continuation-in-part of International Application No. PCT/KR2014/009204 having filed on Sep. 30, 2014, which claimed the benefit of Korean Patent Application No. 10-2013-0117527 filed Oct. 1, 2013, the disclosures of each of which are incorporated herein by reference.

REFERENCE TO A SEQUENCE LISTING

This application contains a Sequence Listing submitted electronically as a text file by EFS-Web. The text file, named "Sequence Listing", has a size in bytes of 4 KB, and was recorded on Mar. 29, 2016. The information contained in the text file is incorporated herein by reference in its entirety pursuant to 37 CFR § 1.52(e) (5).

BACKGROUND OF THE INVENTION

1. Field of the Invention

The present invention relates to a pharmaceutical composition for treating cancer, containing cytochrome b5 reductase 3 (CYB5R3) protein as an active ingredient.

2. Description of the Related Art

In spite of all the efforts made by human beings over the past decades, cancer is still one of incurable diseases. Cancer is one of such diseases that threaten human health most seriously, which is caused by unlimited, uncontrollable proliferation and immortalization of cells resulted from a series of mutation. Many biochemical mechanisms involved in cancer have been disclosed, and thereafter various therapeutic agents have been developed. However, none of them are yet a fundamental treatment.

Therefore, it is a continuous request to identify in vivo molecules involved in cancer and to develop a novel drug targeting the said molecules. To improve the therapeutic effect, combinations of some of the drugs have been tried. According to the remarkable advancement in the fields of cancer cell biology, medicinal chemistry, etc., many anti-cancer agents have been developed, which are exemplified by Taxol, rapamycin, and 17-allylaminogeldanamycin (17-AAG). In addition, a novel anti-cancer agent, Gleevec, characterized by a novel functional mechanism is now under the development.

Drugs designed to suppress cancer metastasis are largely functioning to inhibit the function of adhesion molecules including integrin family such as vitronectin, laminin, and fibronectin, which are major components of the extracellular matrix, or to inhibit matrix metalloproteinase (MMP) and collagenase IV (Cancer Research 53, 2087-2091, 1993). Major targets of the drugs to suppress cancer metastasis are as follows; Src, focal adhesion kinase, integrin receptor, vascular endothelial growth factor receptor (VEGF receptor), epidermal growth factor receptor (EGF receptor), Her-2/neu, c-Met, Ras/Rac GTPases, Raf kinase, farnesyl diphosphate synthase, and matrix metalloproteases.

Hypoxia-inducible factor-1 (HIF-1) is a transcription factor induced in hypoxia, which is known as the most important molecule for regulating the adaptation of cancer cells to the hypoxic condition. In particular, the level of HIF-1α protein is closely related to the prognosis of cancer patients. HIF-1 is activated by the stimulation of cancer cell growth factor, hypoxic condition, the activation of oncogene, or the inactivation of tumor suppressor gene such as pVHL. The activated HIF-1 induces the expressions of the genes such as hexokinase 2, glucose transporter 1, erythropoietin, IGF-2, endoglin, VEGFA, MMP-2, uPAR, and MDR1, and as a result the resistance against apoptosis, angiogenesis, cell proliferation, cell migration or metastasis, and cell invasion are all increased, leading to the malignance of cancer cells.

Cytochrome b5 reductase 3 (CYB5R3) exists as binding to endoplasmic reticulum membranes, mitochondrial membranes, and other membranes or as dissolved in erythrocytes. CYB5R3 in erythrocytes is involved in the reduction of methemoglobin. The mutation in CYB5R3 gene induces methemoglobinemias, in which the concentration of methemoglobin is excessively high in blood, resulting in reduction of oxygen delivery to lead to cyanosis and hypoxia. CYB5R3 in membranes is composed of membrane-bound domain and active domain, which is known to be involved in the elongation and desaturation of fatty acid, cholesterol biosynthesis, and drug metabolism. Therefore, studies to develop a diagnostic and therapeutic composition using CYB5R3 have been actively undergoing.

PCT/NL2007/000112 describes that the expression of CYB5R3 is expected to be sensitive to anti-estrogen agent in breast cancer patient. Therefore, CYB5R3 can be useful as a component in diagnostic kit for the anti-estrogen treatment because CYB5R3 could used as an index to predict the tamoxifen-resistance in breast cancer patients. In addition, LEE et al reported that CYB5R3 called as diaphorase 1 was up-regulated in a lung cancer mouse model transformed with K-ras so that CYB5R3 could be used as a marker for diagnosis or prevention of cancer (LEE et al, *Int. J. Oncol.,* 34: 161-172, 2009). However, there has been no report explaining the relation between HIF-1α and CYB5R3 and concerning a pharmaceutical composition for inhibiting cancer using the same.

Thus, the present inventors tried to disclose the cancer inhibiting effect of CYB5R3. As a result, the inventors confirmed that the expression of HIF-1α expression was significantly reduced in the cancer cells by over-expressing CYB5R3, resulting in the inhibition of cancer cell growth and in vivo tumor growth. They further confirmed thereafter that CYB5R3 could be useful as an active ingredient of a pharmaceutical composition for treating cancer, leading to the completion of the present invention.

SUMMARY OF THE INVENTION

It is an object of the present invention to provide a pharmaceutical composition for treating cancer comprising cytochrome b5 reductase 3 (CYB5R3) gene or protein as an active ingredient.

To achieve the above object, the present invention provides a pharmaceutical composition for treating cancer comprising CYB5R3 gene or protein as an active ingredient.

The present invention also provides a method for treating cancer containing the step of administering CYB5R3 protein to a subject in need.

The present invention also provides a use of CYB5R3 protein as an active ingredient of a pharmaceutical composition for treating cancer.

The present invention also provides a pharmaceutical composition for treating cancer which comprises the vector containing the polynucleotide encoding CYB5R3 protein or the cell containing the vector as an active ingredient.

The present invention also provides a method for treating cancer containing the step of administering the vector containing the polynucleotide encoding CYB5R3 protein or the cell containing the said vector to a subject in need.

The present invention also provides a use of the vector containing the polynucleotide encoding CYB5R3 protein or the cell containing the said vector as an active ingredient of a pharmaceutical composition for treating cancer.

The present invention also provides a method for detecting a protein in order to provide information necessary for the diagnosis of cancer, comprising the following steps:

1) measuring the expression of CYB5R3 protein in a sample originated from the test subject of the experimental group;

2) comparing the CYB5R3 protein expression measured in step 1) with that of the normal sample of the control; and 3) determining a risk of cancer outbreak by the decrease of the CYB5R3 protein expression, compared with that of the control.

In addition, the present invention provides a method for screening an anticancer agent candidate comprising the following steps:

1) treating a test compound or a composition to the cell line expressing CYB5R3 protein;

2) measuring the CYB5R3 protein expression in the cell line treated in step 1); and 3) selecting a test compound or a composition that could increase the CYB5R3 protein expression in the cell line of step 2), compared with the control cell line non-treated with the test compound or the composition.

Advantageous Effect

Over-expression of CYB5R3 in cancer cells results in significant reduction of HIF-1α expression, which leads inhibition of growth of cancer cells and vivo tumor growth and metastasis. Therefore, the CYB5R3 gene or protein of the present invention could be efficiently used as an active ingredient of a pharmaceutical composition for treating cancer.

BRIEF DESCRIPTION OF THE DRAWINGS

The application of the preferred embodiments of the present invention is best understood with reference to the accompanying drawings, wherein:

FIG. 1 is a diagram illustrating the expression of cytochrome b5 reductase 3 (CYB5R3) protein in various cancer cell lines.

FIG. 2 is a diagram illustrating the expression of CYB5R3 in the colon cancer tissue.

FIG. 3 is a diagram illustrating the expression of hypoxia-inducible factor-1α (HIF-1α) by CYB5R3 knockdown in the cancer cell line.

FIG. 4A and FIG. 4B is a set of diagrams illustrating the expression of HIF-1α in the cancer cell line according to the over-expression of CYB5R3;

FIG. 4A presents the map of the vector used for the over-expression of CYB5R3; and FIG. 4B presents the expressions of CYB5R3 and HIF-1α in the cancer cells over-expressing CYB5R3.

FIG. 5A and FIG. 5B is a set of diagrams illustrating the oxygen consumption rate (OCR) of mitochondria in the cancer cells over-expressing CYB5R3;

FIG. 5A presents the changes in the basal respiration rate and the maximum respiration rate of the cancer cells over-expressing CYB5R3; and FIG. 5B presents the decrease of the total respiration rate of the cancer cells over-expressing CYB5R3.

FIG. 6A and FIG. 6B is a set of diagrams illustrating the effect of CYB5R3 over-expression on growth inhibition of cancer cells;

FIG. 6A presents the over-expression of CYB5R3 in HCT116 cell line depending on the amount of the vector DNA used to induce the over-expression of CYB5R3; and FIG. 6B presents the effect of CYB5R3 over-expression on growth inhibition of cancer cells depending on the amount of the vector DNA used to induce the over-expression of CYB5R3.

FIG. 7 is a diagram illustrating the comparison of the expressions of CYB5R3 and HIF-1α protein in the cells over-expressing CYB5R3 under the normoxic and hypoxic condition.

FIG. 8A is a diagram illustrating the effect of CYB5R3 overexpression on tumor growth inhibition in the mouse xenograft assay.

FIG. 8B presents the tumor growth over the time in the mouse transplanted with cells overexpressing CYB5R3; and FIG. 8C presents the weight of the tumor 17 days after injection of cancer cells overexpressing CYB5R3.

FIG. 9 presents the effect of CYB5R3 over-expression using the adenovirus over-expressing CYB5R3.

FIG. 10A and FIG. 10B presents the effect of CYB5R3 over-expression in the cells infected with adenovirus on the inhibition of HIF-1α expression (FIG. 10A) and cell growth (FIG. 10B).

FIGS. 11A and 11B present the effect of CYB5R3 over-expression in the cells infected with adenovirus over-expressing CYB5R3 on HIF-1α expression inhibition and cell growth inhibition in various cell lines.

FIG. 12A and FIG. 12B presents the tumor growth over the time (FIG. 12A) and the tumor volume, body weight, tumor weight (FIG. 12B) in ex vivo mouse xenograft model using the adenovirus over-expressing CYB5R3.

DESCRIPTION OF THE PREFERRED EMBODIMENTS

Hereinafter, the present invention is described in detail.

The present invention provides a pharmaceutical composition for treating cancer comprising cytochrome b5 reductase 3 (CYB5R3) protein as an active ingredient.

The present invention also provides a method for treating cancer containing the step of administering CYB5R3 protein to a subject in need.

The present invention also provides a pharmaceutical composition for treating cancer which comprises the vector containing the polynucleotide encoding CYB5R3 protein or the cell containing the vector as an active ingredient.

The present invention also provides a method for treating cancer containing the step of administering the vector containing the polynucleotide encoding CYB5R3 protein or the cell containing the said vector to a subject in need.

The present invention also provides a use of the vector containing the polynucleotide encoding CYB5R3 protein or the cell containing the said vector as an active ingredient of a pharmaceutical composition for treating cancer.

The CYB5R3 protein fragment is preferably composed of one of the amino acid sequences selected from those amino acid sequences in 1)~3) below, but not always limited thereto:

1) the amino acid sequence represented by SEQ. ID. NO: 1 (Genebank Accession No: AAH04821);
2) the amino acid sequence represented by a part of the sequence represented by SEQ. ID. NO: 1; and
3) the amino acid sequence showing at least 80% homology with the sequence represented by SEQ. ID. NO: 1.

The CYB5R3 protein herein preferably inhibits hypoxia-inducible factor-1 (HIF-1) in cancer cells, but not always limited thereto.

The cancer herein is preferably one or more cancers selected from the group consisting of melanoma, small cell lung cancer, non-small cell lung cancer, glioma, liver cancer, thyroid gland tumor, stomach cancer, prostate cancer, breast cancer, ovarian cancer, bladder cancer, lung cancer, colorectal cancer, glioblastoma, endometrical cancer, kidney cancer, colon cancer, pancreatic cancer, esophageal carcinoma, head & neck cancer, mesothelioma, sarcoma, gallbladder cancer, small intestinal adenocarcinoma, child carcinoma, and epidermoid carcinoma, and more preferably one or more cancers selected from the group consisting of colorectal cancer, liver cancer, stomach cancer, breast cancer, pancreatic cancer, prostate cancer, lung cancer, and kidney cancer, and most preferably colorectal cancer, but not always limited thereto.

The vector herein is preferably the vector containing a linear DNA expressed in human or animal cells, a plasmid vector, a vector containing the viral expression vector, or a recombinant virus vector including a recombinant retrovirus vector, a recombinant adenovirus vector, a recombinant adeno-associated virus (AAV) vector, a recombinant herpes simplex virus vector, a recombinant vaccinia virus, or a recombinant lentivirus vector, but not always limited thereto.

The cell herein is preferably selected from the group consisting of hematopoietic stem cells, dendritic cells, autologous tumor cells, and established tumor cells, but not always limited thereto.

In a preferred embodiment of the present invention, the expressions of CYB5R3 and HIF-1α in a cancer cell line were investigated. As a result, the CYB5R3 expression was significantly reduced in the cancer cell line and the cancer tissues, compared with in the normal cells. In the meantime, the HIF-1α expression was significantly increased, suggesting that the HIF-1α had the inverse correlation with the CYB5R3 (see FIGS. 1 and 2).

The present inventors also investigated the expression of HIF-1α protein in the cancer cell line wherein CYB5R3 protein was down-regulated or up-regulated. As a result, when HIF-1α was induced under hypoxic condition, CYB5R3 expression was suppressed. In the meantime, the expression of HIF-1α in the cell line over-expressing CYB5R3 was inhibited (see FIGS. 3 and 4).

The present inventors investigated the inhibitory effect of CYB5R3 on the cancer cell growth. As a result, it was confirmed that the oxygen consumption rate (OCR) of mitochondria and the cancer cell growth were significantly inhibited in the cancer cells over-expressing CYB5R3 (see FIGS. 5 and 6).

The present inventors also investigated the inhibitory effect of CYB5R3 on the cancer cell growth effect in vivo. As a result, it was confirmed that the tumor size and weight were effectively reduced when CYB5R3 over-expression was introduced using stable cell line or adenovirus infection in the mouse xenograft model (see Tables 2 and 3, and FIGS. 8 and 9, and FIG. 12).

In conclusion, in the present invention, over-expression of CYB5R3 significantly reduced the expression of HIF-1α via suppression of mitochondrial respiration, resulting in anti-tumor efficacy in vitro and in vivo. Therefore, the CYB5R3 gene or protein of the present invention can be efficiently used as an active ingredient of a pharmaceutical composition for treating cancer.

The composition of the present invention contains preferably 0.05~500 mg of the vector containing the polynucleotide encoding CYB5R3, and more preferably 0.1~300 mg of the same. The composition of the present invention contains preferably $10^3$~$10^{12}$ IU (10~$10^{10}$ PFU) of the recombinant virus containing the polynucleotide encoding C12orf59 originated peptide, and more preferably $10^5$~$10^{10}$ IU of the same, but not always limited thereto.

The composition of the present invention contains preferably $10^3$~$10^8$ of the cells containing the polynucleotide encoding CYB5R3 protein, and more preferably $10^4$~$10^7$ of the same, but not always limited thereto.

In the composition comprising the vector containing the polynucleotide encoding CYB5R3 protein or the cell containing the vector, the effective dosage of the vector is 0.05~12.5 mg/kg and preferably 0.1~10 mg/kg, the effective dosage of the recombinant virus vector is $10^7$~$10^{11}$ virus particles ($10^5$~$10^9$ IU)/kg and preferably $10^8$~$10^{10}$ virus particles ($10^6$~$10^8$ IU)/kg, and the effective dosage of the cell is $10^3$~$10^6$ cells/kg and preferably $10^2$~$10^3$ cells/kg. The composition can be administered 2~3 times a day. The dosage and composition are not limited to the above, and can be adjusted according to the patient's condition and the severity of nerve disorder.

The present invention also provides a method for detecting a protein in order to provide information necessary for the diagnosis of cancer, comprising the following steps:

1) measuring the expression of CYB5R3 protein in a sample originated from the test subject of the experimental group;
2) comparing the CYB5R3 protein expression measured in step 1) with that of the normal sample of the control; and
3) determining a risk of cancer by the decrease of the CYB5R3 protein expression, compared with that of the control.

The expression of CYB5R3 protein in step 1) is preferably measured by one of the detection methods selected from the group consisting of Western blotting, enzyme-linked immunosorbent assay (ELISA), immunohistochemical staining, immunoprecipitation, and immunofluorescence, but not always limited thereto.

In addition, the present invention provides a method for screening an anticancer agent candidate comprising the following steps:

1) treating a test compound or a composition to the cell line expressing CYB5R3 protein;
2) measuring the CYB5R3 protein expression in the cell line treated in step 1); and
3) selecting a test compound or a composition that could increase the CYB5R3 protein expression in the cell line of step 2), compared with the control cell line non-treated with the test compound or the composition.

The CYB5R3 of the present invention is significantly down-regulated in the cancer cell line or cancer tissues, compared with in the normal cell line or normal tissues. In the meantime, the HIF-1α expression is significantly reduced in the cell line over-expressing CYB5R3. Therefore, the CYB5R3 protein of the invention can be efficiently used for the method to treat cancer patients and for the method to provide information necessary for the diagnosis of cancer.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Expressions of Cytochrome b5 Reductase 3 (CYB5R3) and Hypoxia-Inducible Factor-1 (HIF-1) in Cancer Cell Lines <1-1> Cancer Cell Culture and Induction of HIF-1 Accumulation Various cancer cell lines were cultured to accomplish examples of the invention.

Particularly, various human cancer cell lines, shown in Table 1 below, were purchased from ATCC (American Type Culture Collection). RPMI1640 supplemented with 5% fetal bovine serum (FBS) was loaded in a cell culture vessel, to which the cultured cells were inoculated at the density of $5 \times 10^5$ cells/ml, followed by culture in a 37° C. 5% $CO_2$ incubator for 24 hours. To induce the accumulation of HIF-1α, the cells were further cultured for 12 more hours under hypoxic condition (1% oxygen, 94% nitrogen, and 5% $CO_2$).

TABLE 1

| Various cancer cell lines | | |
| --- | --- | --- |
| Origin | Name | ATCC No. |
| Colorectal cancer cell line | DLD-1 | CCL-221 |
|  | HCC2998 | CCL-119 |
|  | HCT116 | CCL-247 |
|  | KM12 |  |
|  | LoVo | CCL-229 |
|  | SW620 | CCL-227 |
|  | WiDr | CCL-218 |
| Breast cancer cell line | MCF-7 | HTB-22 |
| Pancreatic cancer cell line | MIA-Paca2 | CRL-1420 |
| Prostate cancer cell line | PC-3 | CRL-1435 |
| Lung cancer cell line | A549 | CCL-185 |
| Kidney cancer cell line | Caki-1 | HTB-46 |
|  | 786-O | CRL-1932 |
|  | RCC-4 |  |
| Normal cell line | WI-38 | CCL-75 |

<1-2> Expressions of CYB5R3 and HIF-1α Cancer Cell Line Under Hypoxic Condition

To confirm the expressions of HIF-1α and CYB5R3 in the cancer cell line, a cell extract was obtained from the cancer cell line under hypoxic condition, followed by Western blotting.

Particularly, the HIF-1α accumulation induced various cancer cell lines were obtained in Example <1-1>. Each cell line was lysed by using RIPA buffer (radioimmuno precipitation assay buffer; Cell Signaling Technology, USA) and as a result each cell extract was obtained. 30 μg of the obtained each cell extract was loaded on SDS-PAGE (sodium dodecyl sulfate-polyacrylamide gel electrophoresis) and then transferred on polyvinylidene fluoride membrane. The membrane was reacted with CYB5R3 antibody (Santa Cruz Biotechnology, USA) and HRP-labeled secondary antibody (Amersham-Pharmacia, USA) stepwise to confirm the expression of CYB5R3. The expression of HIF-1α was also confirmed by using HIF-1α antibody (R,D Systems) and HRP-labeled secondary antibody by the same manner as described above. For the control, the expression of GAPDH (glyceradehyde 3-phosphate dehydrogenase) or actin was measured by using rabbit polyclonal GAPDH antibody (Ab Frontier, Korea) or rabbit polyclonal β-actin antibody (Cell Signaling Technology, USA) by the same manner as described above.

As a result, as shown in FIG. 1, the expression of CYB5R3 was significantly reduced in such cell lines as colorectal cancer, breast cancer, pancreatic cancer, prostate cancer, lung cancer, and kidney cancer cell lines, compared with the normal cell line WI-38. In the meantime, the expression of HIF-1α was significantly increased, suggesting that HIF-1α had the inverse correlation with CYB5R3 (FIG. 1).

Example 2

Expressions of CYB5R3 in Cancer Tissue

To investigate the expression of CYB5R3 protein in cancer tissues, immunohistochemistry staining was performed with the colorectal cancer tissues.

Precisely, the samples for the diagnosis were provided from The Catholic University of Korea Daejeon Saint Mary Hospital (Korea), which were then fixed in formalin to prepare paraffin blocks of 20 colorectal cancer tissues. Those paraffin blocks were treated with xylene to eliminate paraffin from the paraffin section. The blocks were heated at 100° C. to recover the antigen, followed by washing with phosphate buffered saline (PBS) three times. The anti-CYB5R3 antibody (Sigma-Aldrich, USA) diluted with the antibody dilution buffer (Covance, USA) at the ratio of 1:200 was used as the primary antibody and the biotin-conjugated antibody was used as the secondary antibody to measure the level of CYB5R3 by using Streptavidin Biotin Universal Detection System (Immunotech, Finland) according to the manufacturer's protocol. Color development was induced with AEC Chromogen Kit (Immunotech, Finland). For the positive control, immunohistostaining was performed with the normal tissue WI-38 by the same manner as described above and the color strength was compared.

As a result, as shown in FIG. 2, the cells comprising CYB5R3 were expressed increasingly in the glandular structures in the normal tissues, while the cells expressing CYB5R3 were significantly reduced and the distorted glands were observed at the same time in the colorectal cancer tissues (FIG. 2).

Example 3

Expression of HIF-1α by CYB5R3 Knockdown in Cancer Cell Lines

<3-1> Expression of HIF-1α in the CYB5R3 Suppressed Cancer Cell Line

To investigate the interrelation between CYB5R3 and HIF-1α expression, the expression of HIF-1α protein was measured in the cancer cells wherein the CYB5R3 expression was suppressed.

Particularly, 20 nM of CYB5R3 siRNA (Thermo Co.; Cat. No: siGENOME human CYB5R3 (1727) siRNA SMART pool) was treated with Dharmafect (thermo Co.), with which the colon cancer cell line HCT116 was transfected. The transfected cell line was cultured in DMEM (Dulbecco's Modified Eagle's Medium) supplemented with 5% FBS for 24 hours. To induce the accumulation of HIF-1α, the cell line was cultured under hypoxic condition (1% oxygen, 94% nitrogen, and 5% $CO_2$) for 12 hours. The expressions of CYB5R3 and HIF-1α protein were measured by the same manner as described in Example <1-2>. For the negative control, the transfected cell line was cultured in the presence of 20% oxygen and the expressions of CYB5R3 and HIF-1α protein were measured by the same manner as described above. As the control protein, the rabbit polyclonal GAPDH antibody (Ab Frontier, Korea) was used and the expression of GAPDH (glyceraldehyde 3-phosphate dehydrogenase) was measured by the same manner as described above.

As a result, as shown in FIG. 3, the negative control under normoxic condition did not express HIF-1α. When CYB5R3 expression was suppressed by CYB5R3 knockdown, HIF-1α expression increased under hypoxic condition, (FIG. 3).

<3-2> Expression of HIF-1α in the Cancer Cell Line Over-Expressing CYB5R3

To investigate the interrelation between CYB5R3 and HIF-1α expression, CYB5R3 was over-expressed in a cancer cell line and the HIF-1α expression therein was measured.

Particularly, pCMV-AC-CYB5R3 (FIG. 4a; Origin, USA), the pCMV6-AV vector containing CYB5R3 gene, was amplified. 4 μg of the said vector and lipofectamine 2000 (Invitrogen, Carlsbad, Calif.) were loaded in a 60 mm dish containing DMEM supplemented with 5% FBS, to which $4 \times 10^5$ cells of the colorectal cancer cell line HCT116 were inoculated, followed by culture for 24 hours for DNA transfection. Then, in order to induce the accumulation of HIF-1α, the cell line was cultured under hypoxic condition (1% oxygen, 94% nitrogen, and 5% $CO_2$) for 12 hours. The expressions of CYB5R3 and HIF-1α protein were measured by the same manner as described in Example <1-2>. For the negative control, the transfected cell line was cultured in the presence of 20% oxygen and the expressions of CYB5R3 and HIF-1α protein were measured by the same manner as described above. As the control protein, the rabbit polyclonal GAPDH antibody (Ab Frontier, Korea) was used and the expression of GAPDH (glyceraldehyde 3-phosphate dehydrogenase) was measured by the same manner as described above. The expressions of CYB5R3 and HIF-1α protein were measured by the same manner as described in Example <2-1>.

As a result, as shown in FIG. 4B, as the expression of CYB5R3 increased by CYB5R3 over-expression, the expression of HIF-1α was reduced under hypoxic condition in colorectal cancer cell line (FIG. 4B).

Example 4

Inhibitory Effect of CYB5R3 on Cancer Cell Growth

<4-1> Oxygen Consumption Rate (OCR) of Mitochondria in the Cancer Cell Line Over-Expressing CYB5R3

To investigate the effect of CYB5R3 on the growth inhibition of cancer cells, the oxygen consumption rate of mitochondria was measured in the cancer cells over-expressing CYB5R3.

Particularly, the colon cancer cell line HCT116 transiently over-expressing CYB5R3 was cultured by the same manner as described in Example <3-2>. $1 \times 10^5$ cultured cells were further cultured in XF24 cell culture plate for 2 hours. The medium was replaced with XF measuring medium, followed by culture in a $CO_2$-free incubator for 1 hour. OCR was measured by using XF24 extracellular flux analyzer (Seahorse Bioscience, USA) three times. The ATP synthesis inhibitor, oligomycin, was treated thereto at the concentration of 1 μM. Then, OCR was measured three times again. The chemical uncoupler, carbonylcyanide p-trifluoromethoxyphenylhydrazone, was treated thereto at the concentration of 0.5 μM, and then OCR was measured three times. The electron transport system inhibitor, rotenone, was treated thereto at the concentration of 1 μM, and then OCR was measured twice. 1 μM of antimycin A was treated thereto and OCR was measured twice again.

As a result, as shown in FIG. 5, both basal respiration and maximum respiration were significantly reduced in the cells overexpressing CYB5R3 (FIG. 5A). In addition, the total OCR in the cell line over-expressing CYB5R3 was reduced by 40% (FIG. 5B).

<4-2> Growth Inhibition of the Cancer Cell Line Over-Expressing CYB5R3

To investigate the inhibiting effect of CYB5R3 on cell growth, survival of the cancer cell line over-expressing CYB5R3 was measured.

Particularly, pCMV-AC-CYB5R3 (Origin, USA), the pCMV6-AV vector containing CYB5R3 gene, was amplified. The colorectal cancer cell line HCT116 was cultured in DMEM supplemented with 0.5 μg, 1 μg, or 2 μg of the said vector and lipofectamine 2000 (Invitrogen, Carlsbad, Calif., USA) for 24 hours for DNA transfection. Upon completion of the culture, the HCT116 cell line transfected with DNA was distributed in a 96 well plate at the density of $3 \times 10^3$ cells/100 μl, followed by culture in a 37° C. 5% $CO_2$ incubator for 72 hours. The cells were fixed with 4% formaldehyde at room temperature for 1 hour and washed with PBS. Then, the cells were stained with 0.5% methylene blue (50 μl/well) at room temperature for 1 hour. The cells were washed with distilled water and dried. 100 μl of 0.06 N HCl was distributed thereto and the cells were well-mixed with it at room temperature for 10 minutes. $OD_{600}$ was measured by using ELISA plate reader to confirm the cell growth.

As a result, as shown in FIG. 6, CYB5R3 protein expression was transiently increased by transfection of pCMV-AC-CYB5R3 dose-dependently. Moreover, the growth of cancer cells was suppressed by CYB5R3 overexpression in a dose-dependent manner in HCT116 cell line (FIGS. 6A and 6B).

Example 5

The Effect of CYB5R3 on In Vivo Tumor Growth

<5-1> Construction of the Cell Line Over-Expressing CYB5R3

To prepare the cell line over-expressing CYB5R3, HCT116 cell line over-expressing CYB5R3 stably was constructed.

Particularly, $4 \times 10^5$ HCT116 cells were inoculated in a 60 mm dish containing DMEM supplemented with 5% FBS, followed by culture in a 37° C. 5% $CO_2$ incubator for 24 hours. 4 µg of pCMV-AV-CYB5R3 (Origin, USA), the PCMV6-AV vector containing CYB5R3 gene, and lipofectamine 2000 (Invitrogen, Carlsbad, Calif.) were added thereto, followed by culture at 37° C. for 48 hours for DNA transfection. The HCT116 cells were cultured in DMEM (Dulbecco's Modified Eagle's Medium) supplemented with 0.5 mg/ml of G418 (Gibco, USA) for 2 weeks. The cells transfected with the vector for CYB5R3 over-expression were selected. The single colony of those cells was obtained and cultured. The expression of CYB5R3 was investigated by the same manner as described in Example <1-2>. Thereafter, the HCT cell line over-expressing CYB5R3 stably was selected. For the negative control, the expression vector pCMV-AC (Origin, USA) that did not contain CYB5R3 gene was introduced in HCT116 cell line and stable cell line was constructed by the same manner as described above.

As a result, as shown in FIG. 7, the HCT116 cell line over-expressing CYB5R3 stably was collected and the decrease of HIF-1α expression was confirmed in the said HCT116 cell line under hypoxic condition (FIG. 7).

<5-2> Inhibitory Effect of CYB5R3 on In Vivo Tumor Growth

To investigate the effect of CYB5R3 on the in vivo tumor growth, the cell line over-expressing CYB5R3 was used in in vivo xenograft model and the changes of the tumor size therein were confirmed.

Particularly, the HCT116 cell line over-expressing CYB5R3 prepared in Example <5-1> was treated with trypsin and collected. The cells were washed with serum-free medium and diluted at the concentration of $5 \times 10^7$ cells/ml. The diluted cells were injected through the side of 5 female Balb/c specific pathogen free (SPF) nude mice at 6 weeks (SLC-Central Lab. Animal Inc., Korea) via subcutaneous injection to complete the tumor cell transplantation ($1 \times 10^7$ cells/200 µl). On day 3, 5, 7, 12, 14, and 17 after the transplantation, the weight of each nude mouse and the size and the growth of tumor were measured by using the mathematical formula 1 of the below. On day 17 after the transplantation, the animals were sacrificed and the weight and the size of tumor were measured to investigate the formation and the growth of tumor. The tumor growth in the negative control <5-1> was measured by the same manner as described above.

Tumor Size $(mm^2)$=(length×area×height)/2 [Mathematical Formula 1]

As a result, as shown in Tables 2 and 3, and in FIG. 8, the body weight of the mouse was not changed significantly after the transplantation of tumor (Table 2). Compared with the control, in the mouse introduced with the HCT116 cell line over-expressing CYB5R3, the tumor growth was about 65% inhibited (FIG. 8A, 8B and Table 3). On the 17th day after the tumor transplantation, the tumor weight was 11.0±32.1 mg, which was 48% lower than that of the negative control (210.0±36.1 mg) (FIG. 8C).

TABLE 2

Changes of body weight in the mouse transplanted with the CYB5R3 over-expressing cells and tumor

| Time (day) | Weight (g) |
|---|---|
| 3 | 19.0 ± 0.4 |
| 5 | 19.5 ± 0.4 |
| 7 | 19.5 ± 0.1 |
| 10 | 18.7 ± 0.6 |
| 12 | 18.8 ± 0.3 |
| 14 | 18.6 ± 0.3 |
| 17 | 18.3 ± 0.4 |

TABLE 3

Inhibitory effect of CYB5R3 on in vivo tumor growth

| Time (day) | Tumor size (mm 3) | |
|---|---|---|
| | CYB5R3 expression | Negative Control |
| 3 | 32.7 ± 3.7 | 37.3 ± 2.0 |
| 5 | 27.0 ± 7.0 | 46.0 ± 4.6 |
| 7 | 38.9 ± 9.4 | 98.9 ± 33.2 |
| 10 | 65.6 ± 23.0 | 238.9 ± 79.4 |
| 12 | 88.0 ± 31.5 | 360.1 ± 83.4 |
| 14 | 119.0 ± 28.4 | 430.5 ± 117.2 |
| 17 | 216.0 ± 60.1 | 603.2 ± 123.3 |

Example 6

In Vivo Anti-Tumor Efficacy of CYB5R3 Using Adenovirus Overexpressing CYB5R3

<6-1> Construction of CYB5R3 Over-Expressing Adenovirus

The adenovirus over-expressing CYB5R3 was constructed by the homologous recombination of the adenovirus backbone vector pAD-Easy and the linearized shuttle transfer vector pAdTrack-CMV containing a CYB5R3 gene. The said pAdTrack contains the second independent CMV promoter which facilitates the construction of GFP-trackable virus (GFP is co-expressed when the target gene is expressed) and the monitoring of viral injection efficiency. HCT116 cells were infected with the constructed adenovirus and then the over-expression of CYB5R3 was confirmed (FIG. 9).

<6-2> the Effect of CYB5R3 Over-Expression on HIF-1α in the Colorectal Cancer Cell Line The HIF-1α expression was investigated in the cells infected with adenovirus over-expressing CYB5R3, which was constructed in Example <6-1>. Then, the expression of HIF-1α protein was measured. Particularly, the CYB5R3 over-expressing adenovirus was added to DMEM supplemented with 5% FBS (MOI=2), to which the colorectal cancer cell line HCT116 was loaded ($5 \times 10^5$, 60 mm dish), followed by culture for 36 hours. Then, the cells were cultured under hypoxic condition (1% oxygen, 94% nitrogen, and 5% $CO_2$) for 12 hours. The protein was extracted, and the expressions of CYB5R3 and HIF-1α therein were measured by electrophoresis and Western blotting.

As a result, as shown in FIG. 10(A), it was confirmed that the expression of HIF-1α was suppressed by the over-expression of CYB5R3 in HCT116 cell line.

<6-3> Inhibition of Colorectal Cancer Cell Growth by the Infection of Adenovirus Over-Expressing CYB5R3

The following experiment was performed to investigate the changes of cancer cell growth by the CYB5R3 over-expressing adenovirus. Particularly, the CYB5R3 over-expressing adenovirus was added to DMEM supplemented with 5% FBS (MOI=2), to which the colorectal cancer cell line HCT116 was loaded (5×10$^3$, 96 well plate), followed by culture for 72 hours. Then, the cells were fixed with 10% formalin, and washed with PBS three times. Methylene blue solution was added to each well, followed by reaction for 30 minutes. The plate was washed three times and 0.5% HCl aqueous solution was added thereto, followed by the extraction of the stained methylene blue. Then, $OD_{600}$ was measured to calculate the cell survival rate.

As a result, as shown in FIG. 10(B), it was confirmed that the growth of colorectal cancer cell line was suppressed by the infection of adenovirus over-expressing CYB5R3.

<6-4> Function of the CYB5R3 Over-Expressing Adenovirus in Various Cancer Cell Lines The following experiment was performed to investigate the effect of the said CYB5R3 over-expressing adenovirus on various cancer cell lines. Particularly, the lung cancer cell line A549, the liver cancer cell line HepG2, the pancreatic cancer cell line Mia-paca, the prostate cancer cell line PC-3, the stomach cancer cell line NUGC-3, the uterine cervical cancer cell line HeLa, and the breast cancer cell line MCF7 were infected with the adenovirus over-expressing CYB5R3 under the same condition as described in Example <6-3>.

As a result, as shown in FIGS. 11A and 11B, the expression of HIF-1α and the cell growth were inhibited by the over-expression of CYB5R3, suggesting that CYB5R3 over-expression has an anti-cancer effect on various kinds of tumors.

<6-5> Ex Vivo Tumor Suppressing Effect of CYB5R3 Overexpression Using Adenovirus Over-Expressing CYB5R3

The effect of the CYB5R3 over-expression on tumor growth in vivo using adenovirus was investigated after generating a tumor of colorectal cancer cell line HCT116 in a mouse. When tumor size reached to 50-100 mm$^3$, the adenovirus over-expressing CYB5R3 was administered via local injection to tumor and the change of tumor size in the mouse were observed. Particularly, the colorectal cancer cell line HCT116 was injected through the side of 5 female Balb/c specific pathogen free (SPF) nude mice at 6 weeks of age (SLC-Central Lab. Animal Inc., Korea) via subcutaneous injection to complete the tumor transplantation (1×10$^7$ cells/200 μl). 7 and 10 days after the tumor transplantation, the CYB5R3 over-expressing adenovirus (5×10$^8$ TU) constructed in the above was locally injected to tumor in the mouse. The weight of the mouse and the size of the tumor were measured by using the mathematical formula 1 of the above. 14 days after the virus administration, the mouse was sacrificed and the tumor was taken out, followed by measurement of the weight and the size of the tumor in order to confirm the formation and the growth of tumor. As for the negative control, the mouse was treated with the CYB5R3 non-expressing adenovirus or PBS and the tumor growth was measured by the same manner as described above.

As a result, as shown in FIG. 12, Table 4, and Table 5, a significant body weight change was not observed according to the administration of the adenovirus. There was no significant difference of the tumor sizes between the PBS treated group and the CYB5R3 non-expressing adenovirus (Ad-GFP) treated group. In the meantime, the size of the tumor treated with the CYB5R3 over-expressing adenovirus (Ad-CYB5R3) was reduced about 66%, compared with the negative control (Vehicle) treated with PBS (FIG. 12A). 14 days after virus administration, the weight of the tumor was 250.2±64.6 mg, which was about 62% by the tumor weight of the negative control (645.0±137.9 mg).

TABLE 4

| | Weight (g) | | |
|---|---|---|---|
| Time (Day) | Negative control (Vehicle) | CYB5R3 non-expressing adenovirus (Ad-GFP) | CYB5R3 over-expressing adenovirus (Ad-CYB5R3) |
| 0 | 19.3 ± 0.8 | 19.6 ± 0.9 | 20.3 ± 0.6 |
| 3 | 19.1 ± 0.5 | 19.4 ± 0.7 | 19.9 ± 0.7 |
| 5 | 19.8 ± 0.6 | 19.1 ± 0.7 | 18.7 ± 0.3 |
| 7 | 20.2 ± 0.3 | 19.3 ± 0.4 | 19.9 ± 0.7 |
| 10 | 20.6 ± 0.3 | 19.8 ± 0.6 | 20.9 ± 0.6 |
| 12 | 20.9 ± 0.5 | 20.6 ± 0.7 | 21.4 ± 0.6 |
| 14 | 21.0 ± 0.9 | 21.0 ± 0.7 | 21.3 ± 0.4 |

TABLE 5

| | Tumor volume (mm$^3$) | | |
|---|---|---|---|
| Time (Day) | Negative control (Vehicle) | CYB5R3 non-expressing adenovirus (Ad-GFP) | CYB5R3 over-expressing adenovirus (Ad-CYB5R3) |
| 0 | 65.4 ± 4.5 | 73.4 ± 8.8 | 79.5 ± 8.4 |
| 3 | 128.6 ± 37.1 | 127.7 ± 15.7 | 85.8 ± 5.7 |
| 5 | 228.5 ± 71.7 | 219.1 ± 9.8 | 91.7 ± 21.5 |
| 7 | 350.5 ± 121.9 | 368.2 ± 57.4 | 131.7 ± 28.3 |
| 10 | 738.7 ± 257.6 | 752.4 ± 147.4 | 205.1 ± 69.0 |
| 12 | 946.6 ± 289.3 | 1058.2 ± 172.0 | 299.6 ± 90.0 |
| 14 | 1133.3 ± 339.7 | 1314.9 ± 192.3 | 390.0 ± 102.8 |

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for treating cancer comprising a step of administering a vector containing a polynucleotide encoding cytochrome b5 reductase 3 (CYB5R3) protein or a cell containing the vector to a subject in need of cancer treatment; wherein the CYB5R3 protein is overexpressed and inhibits hypoxia-inducible factor 1 (HIF-1) in cancer cells of the subject, and wherein the cancer is one or more cancers selected from the group consisting of colorectal cancer, liver cancer, stomach cancer, breast cancer, pancreatic cancer, prostate cancer, lung cancer, and kidney cancer.

2. The method for treating cancer according to claim 1, wherein the CYB5R3 protein consists of the amino acid sequence represented by SEQ. ID. NO: 1 (GenBank Accession No: AAH04821).

3. The method for treating cancer according to claim 1, wherein the vector is a linear DNA, a plasmid DNA, or a recombinant virus vector.

4. The method for treating cancer according to claim 3, wherein the recombinant virus is selected from the group consisting of native or modified form of retrovirus, adenovirus, adeno-associated virus, herpes simplex virus, lentivirus, vaccinia virus.

5. The method for treating cancer according to claim 1, wherein the cell is selected from the group consisting of hematopoietic stem cells, dendritic cells, autologous tumor cells, and established tumor cells.

* * * * *

SEQUENCE LISTING

<160> NUMBER OF SEQ ID NOS: 1

<210> SEQ ID NO 1
<211> LENGTH: 301
<212> TYPE: PRT
<213> ORGANISM: Homo sapiens

<400> SEQUENCE: 1

```
Met Gly Ala Gln Leu Ser Thr Leu Gly His Met Val Leu Phe Pro Val
1               5                   10                  15

Trp Phe Leu Tyr Ser Leu Leu Met Lys Leu Phe Gln Arg Ser Thr Pro
                20                  25                  30

Ala Ile Thr Leu Glu Ser Pro Asp Ile Lys Tyr Pro Leu Arg Leu Ile
        35                  40                  45

Asp Arg Glu Ile Ile Ser His Asp Thr Arg Arg Phe Arg Phe Ala Leu
    50                  55                  60

Pro Ser Pro Gln His Ile Leu Gly Leu Pro Val Gly Gln His Ile Tyr
65                  70                  75                  80

Leu Ser Ala Arg Ile Asp Gly Asn Leu Val Val Arg Pro Tyr Thr Pro
                85                  90                  95

Ile Ser Ser Asp Asp Asp Lys Gly Phe Val Asp Leu Val Ile Lys Val
            100                 105                 110

Tyr Phe Lys Asp Thr His Pro Lys Phe Pro Ala Gly Gly Lys Met Ser
        115                 120                 125

Gln Tyr Leu Glu Ser Met Gln Ile Gly Asp Thr Ile Glu Phe Arg Gly
    130                 135                 140

Pro Ser Gly Leu Leu Val Tyr Gln Gly Lys Gly Lys Phe Ala Ile Arg
145                 150                 155                 160

Pro Asp Lys Lys Ser Asn Pro Ile Ile Arg Thr Val Lys Ser Val Gly
            165                 170                 175

Met Ile Ala Gly Gly Thr Gly Ile Thr Pro Met Leu Gln Val Ile Arg
            180                 185                 190

Ala Ile Met Lys Asp Pro Asp Asp His Thr Val Cys His Leu Leu Phe
        195                 200                 205

Ala Asn Gln Thr Glu Lys Asp Ile Leu Leu Arg Pro Glu Leu Glu Glu
210                 215                 220

Leu Arg Asn Lys His Ser Ala Arg Phe Lys Leu Trp Tyr Thr Leu Asp
225                 230                 235                 240

Arg Ala Pro Glu Ala Trp Asp Tyr Gly Gln Gly Phe Val Asn Glu Glu
            245                 250                 255

Met Ile Arg Asp His Leu Pro Pro Pro Glu Glu Glu Pro Leu Val Leu
            260                 265                 270

Met Cys Gly Pro Pro Pro Met Ile Gln Tyr Ala Cys Leu Pro Asn Leu
            275                 280                 285

Asp His Val Gly His Pro Thr Glu Arg Cys Phe Val Phe
    290                 295                 300
```